(12) United States Patent
Miyashita et al.

(10) Patent No.: US 7,252,804 B2
(45) Date of Patent: Aug. 7, 2007

(54) BODY FLUID MEASURING ADAPTER AND BODY FLUID MEASURING UNIT

(75) Inventors: Mariko Miyashita, Nishinomiya (JP); Yuko Taniike, Osaka (JP); Toshihiko Yoshioka, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 259 days.

(21) Appl. No.: 10/472,209

(22) PCT Filed: Mar. 19, 2003

(86) PCT No.: PCT/JP03/03383

§ 371 (c)(1),
(2), (4) Date: Feb. 13, 2004

(87) PCT Pub. No.: WO03/079901

PCT Pub. Date: Oct. 2, 2003

(65) Prior Publication Data

US 2004/0133125 A1 Jul. 8, 2004

(30) Foreign Application Priority Data

Mar. 22, 2002 (JP) .............................. 2002-080329

(51) Int. Cl.
*B01L 9/00* (2006.01)
(52) U.S. Cl. ...................................... 422/104; 600/573

(58) Field of Classification Search ................. 422/104; 211/72; 600/573
See application file for complete search history.

(56) References Cited

U.S. PATENT DOCUMENTS

| 5,120,420 | A |   | 6/1992 | Nankai et al. |
| 5,125,920 | A | * | 6/1992 | Ishida .......................... 604/410 |
| 5,669,502 | A | * | 9/1997 | Ong et al. .................... 206/528 |
| 6,027,459 | A | * | 2/2000 | Shain et al. ................. 600/573 |
| 6,379,317 | B1 |   | 4/2002 | Kintzig et al. |

* cited by examiner

*Primary Examiner*—Jill Warden
*Assistant Examiner*—Natalia Levkovich
(74) *Attorney, Agent, or Firm*—McDermott Will & Emery LLP (57) ABSTRACT

An adaptor for body fluid measurement of the present invention includes a puncture instrument holding section for detachably carrying a puncture instrument for protruding a puncture needle and a measuring instrument holding section for detachably carrying a measuring instrument for analyzing body fluid with a biosensor, the biosensor being attached to the measuring instrument and having a body fluid supply part to which body fluid is supplied. With use of the adaptor, the body fluid can be measured easily and speedily with the puncture instrument and the measuring instrument attached thereto, which are independent from each other. The present invention further provides a measuring instrument including a puncture instrument holding section.

8 Claims, 6 Drawing Sheets

BODY FLUID MEASURING ADAPTER AND BODY FLUID MEASURING UNIT

TECHNICAL FIELD

The present invention relates to an adaptor for body fluid measurement which carries a puncture instrument for protruding a puncture needle and a measuring instrument for analyzing body fluid. The present invention further relates to a body fluid measuring instrument for analyzing body fluid with a puncture instrument carried thereon.

BACKGROUND ART

To diagnosis and treatment of diseases, of very importance are analysis of body fluid such as blood and intercellular fluid of a human body, in particular, detection of the existence of a specific substance in the body fluid or measurement of the contents of substrates contained in the body fluid such as glucose, cholesterol and lactic acid. Here, as an example of the body fluid analysis, explanation is given of measurement of a glucose concentration in blood (hereinafter referred to as a "blood glucose level").

Self-control of the blood glucose level is important for treatment of diabetes. Therefore, a patient of diabetes needs to conduct frequent measurement of his/her blood glucose level to maintain the blood glucose level within a normal range. When the patient measures his/her blood glucose level by himself/herself, the blood glucose level measurement is performed by the following steps.

1) A disposable puncture needle is loaded in advance into a puncture instrument such as a lancet and a disposable biosensor is loaded into a measuring instrument.

2) The puncture instrument is held in a dominant hand and a tip of the puncture instrument is pressed against an arm or a finger of the other hand, and then a puncture needle is protruded to allow blood to ooze out.

3) A measuring instrument is held in the dominant hand in place of the puncture instrument.

4) A body fluid supply part of the biosensor loaded in the measuring instrument is brought into contact with a body part from which blood is allowed to ooze to supply the blood into the biosensor, then the measurement results are waited for.

In this way, the puncture instrument must be replaced with the measuring instrument during the measurement, which is troublesome. Further, if it takes a long time until the blood is supplied to the biosensor after the blood is allowed to ooze, the blood may be dried to deteriorate measurement accuracy.

Under the circumstances, there has been proposed an integrated measuring device in which the puncture instrument and the measuring instrument are united to allow blood collection and measurement. Such an integrated measurement device is sold by Dinabbott under the name of "Sof-Tact", for example.

However, regarding an integrated measuring device of this kind, the puncture needle is held in the device and hence it is difficult to know exactly where the puncture needle protrudes. Therefore, the position to be pricked by the puncture needle cannot be fine adjusted and an area where the blood is allowed to ooze is restricted to relatively large body parts such as arms, which makes blood collection difficult in small parts such as fingertips. There are also problems in that the blood supply to the biosensor cannot be visually checked and the device is large to cause inconvenience in carrying it.

The integrated measuring device conducts the measurement by a succession of operations. Therefore, if a problem occurs in the puncture operation or the blood supply to the sensor, both of the puncture needle and the sensor need to be replaced, which increases the cost. Further, in view of the infection via blood adhered thereto, it is impossible to share the measuring device among many patients at the bedside in an inpatient ward or a diagnosis field.

In view of the above, an object of the present invention is to provide an adaptor for measurement that allows a user to conduct easy and speedy measurement even if a puncture instrument and a measuring instrument are separated.

Further, an object of the present invention is to provide a body fluid measuring instrument attached with a puncture instrument that allows easy and speedy measurement.

DISCLOSURE OF INVENTION

The present invention provides an adaptor for body fluid measurement comprising: a puncture instrument holding section for detachably carrying a puncture instrument for protruding a puncture needle; and a measuring instrument holding section for detachably carrying a measuring instrument for analyzing body fluid with a biosensor, the biosensor being attached to the measuring instrument and having a body fluid supply part to which body fluid is supplied.

Also, the present invention relates to a body fluid measuring instrument comprising a biosensor holding section for holding a biosensor having a body fluid supply part to which body fluid is supplied to analyze the body fluid supplied to the biosensor through the biosensor, wherein the body fluid measuring instrument has a puncture instrument holding section for detachably carrying a puncture instrument for protruding a puncture needle and the puncture instrument holding section is configured such that the puncture needle protruding from the puncture instrument carried by the puncture instrument holding section comes close to the body fluid supply part of the biosensor.

BEST MODE FOR CARRYING OUT THE INVENTION

An adaptor for body fluid measurement according to the present invention utilizes a puncture instrument and a measuring instrument which are independent from each other. Therefore, even if a problem is caused in the puncture or the body fluid collection, there is no need of replacing both of the puncture instrument and the measuring instrument. Moreover, the adaptor has a lot of merits such as the measuring instrument can be shared by merely replacing the puncture instrument.

In a preferred embodiment of the present invention, a puncture instrument holding section and a measuring instrument holding section are arranged to be adjacent to each other to carry the puncture instrument and the measuring instrument in such a manner that a puncture needle protruding from the puncture instrument carried by the puncture instrument holding section comes close to a body fluid supply part of a biosensor of the measuring instrument carried by the measuring instrument holding section.

In a more preferred embodiment of the present invention, the puncture instrument holding section and the measuring instrument holding section are configured such that an axis of the puncture needle of the puncture instrument carried by the puncture instrument holding section intersects with an axis of an inserting direction of the biosensor loaded in the measuring instrument carried by the measuring instrument holding section.

In another preferred embodiment of the present invention, the adaptor includes an adjustment part for adjusting an angle of the puncture instrument holding section with respect to the measuring instrument holding section.

In still another preferred embodiment of the present invention, the puncture instrument holding section has an embrace part for embracing a barrel of the puncture instrument.

It is preferred that the embrace part be made of a cylinder provided with a slit and be configured to have a diameter slightly smaller than a diameter of the barrel of the puncture instrument to embrace the barrel of the puncture instrument by an elastic force thereof.

A body fluid measuring instrument according to a preferred embodiment of the present invention includes a puncture instrument holding section and a biosensor holding section which are configured such that an axis of a puncture needle of the puncture instrument carried by the puncture instrument holding section intersects with an axis of an inserting direction of the biosensor loaded in the biosensor holding section.

Hereinafter, embodiments of the present invention are explained in detail with reference to the drawings.

EMBODIMENT 1

Figure 1:
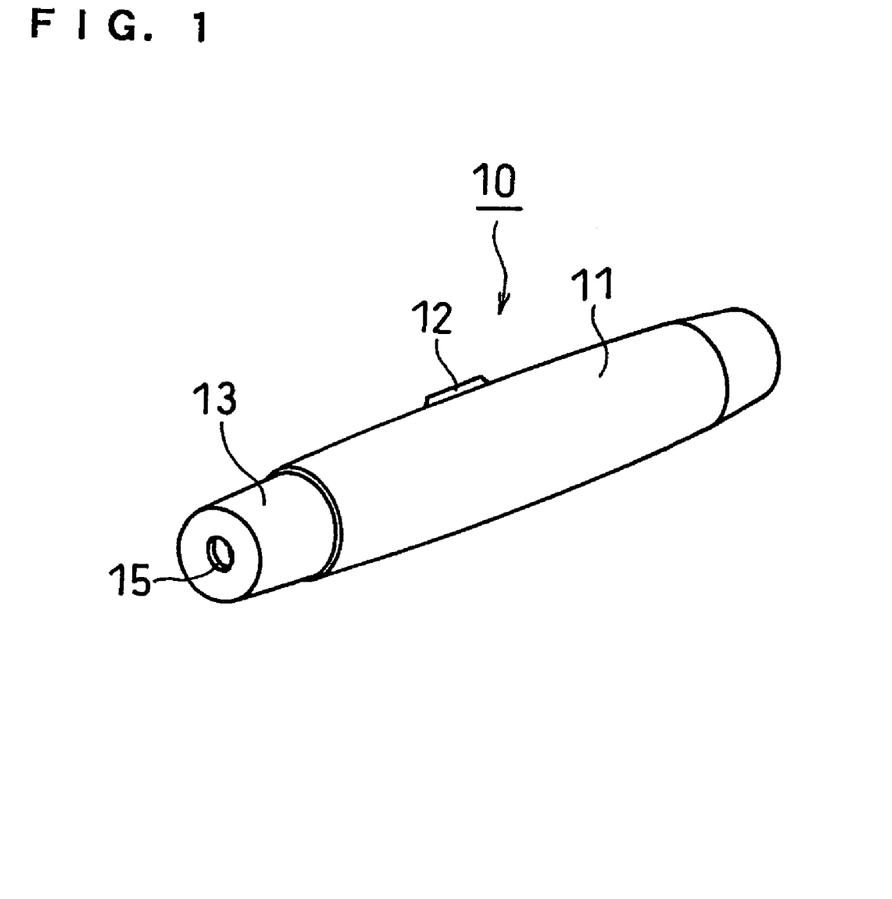
FIG. 1 is an oblique view of a puncture instrument according to Embodiment 1 of the present invention.
Figure 2:
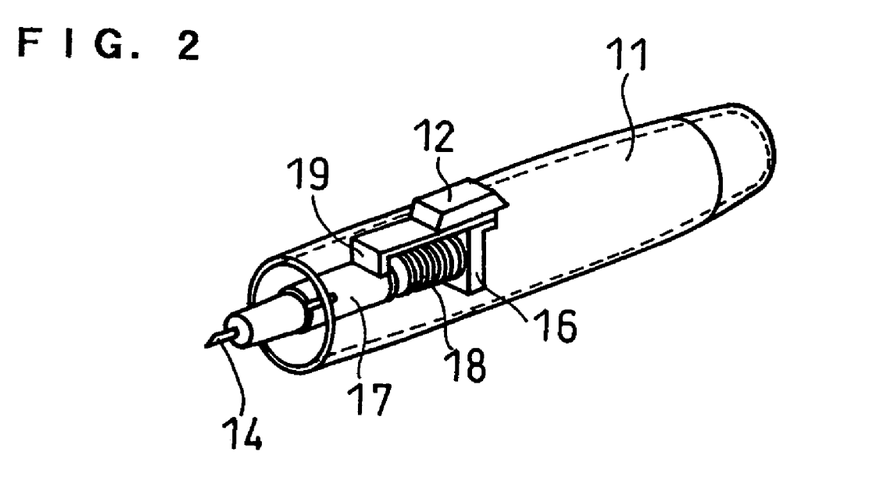
FIG. 2 is an oblique view illustrating an internal structure of the puncture instrument according to Embodiment 1 of the present invention.
Figure 4:
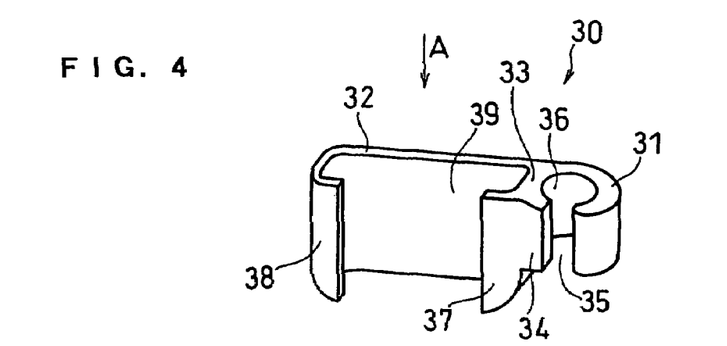
FIG. 4 is an oblique view of an adaptor for measurement according to Embodiment 1 of the present invention.
Figure 5:
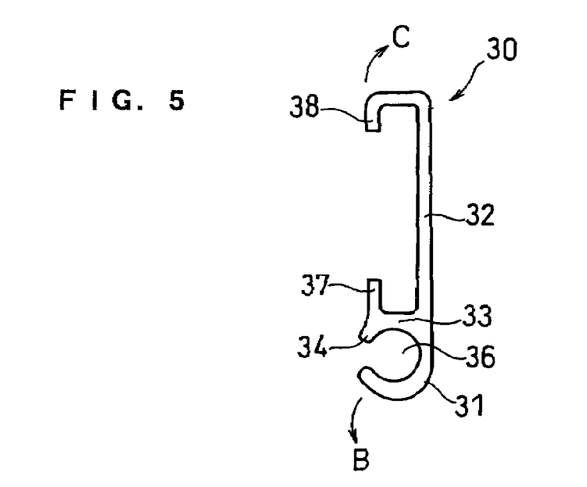
FIG. 5 is a plan view of the adaptor for measurement according to Embodiment 1 of the present invention.
Figure 6:
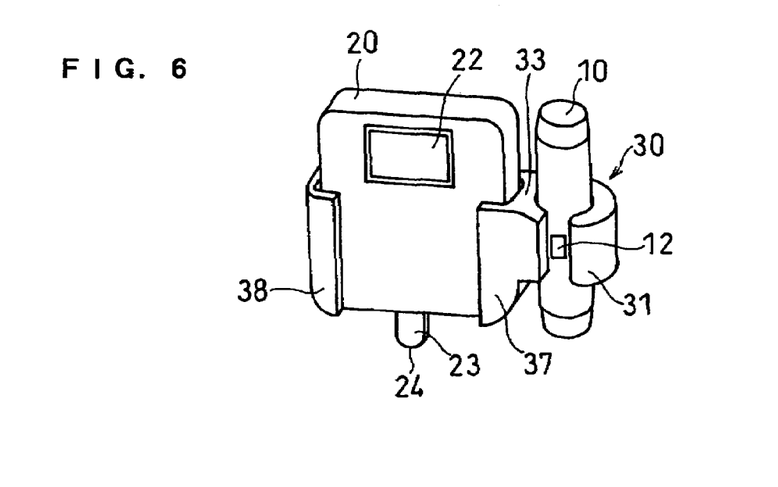
FIG. 6 is an oblique view illustrating a state where the puncture instrument and the measuring instrument are attached to the adaptor for measurement according to Embodiment 1 of the present invention.

FIGS. 4 and 5 show an adaptor for body fluid measurement according to this embodiment. FIG. 6 shows a state where a puncture instrument and a measuring instrument are attached thereto. A puncture instrument 10 used herein includes, as shown in FIGS. 1 and 2, a cylindrical case 11 in which a puncture needle 14 is included, a cover 13 detachably connected to the tip of the case 11 and an operation button 12 projected outside the case 11. In the case 11, there are a needle holder 17 which is mounted on a base 16 and forwardly biased by a spring 18 and a stopper 19 which stops the needle holder 17 by engagement therewith. When the engagement between the stopper 19 and the needle holder 17 is released by operating the button 12, the puncture needle 14 protrudes forward through an aperture 15 in the cover 13 on the tip of the case 11. In loading the puncture needle 14 into the needle holder 17, the cover 13 is detached.

By the puncture needle 14 protruded from the case 11, part of a human body is pricked to allow blood to ooze. FIG. 1 shows a state where the puncture needle 14 loaded into the puncture instrument 10 is accommodated in the case. The puncture needle 14 is replaced after each measurement from the hygienic aspect.

Figure 3:
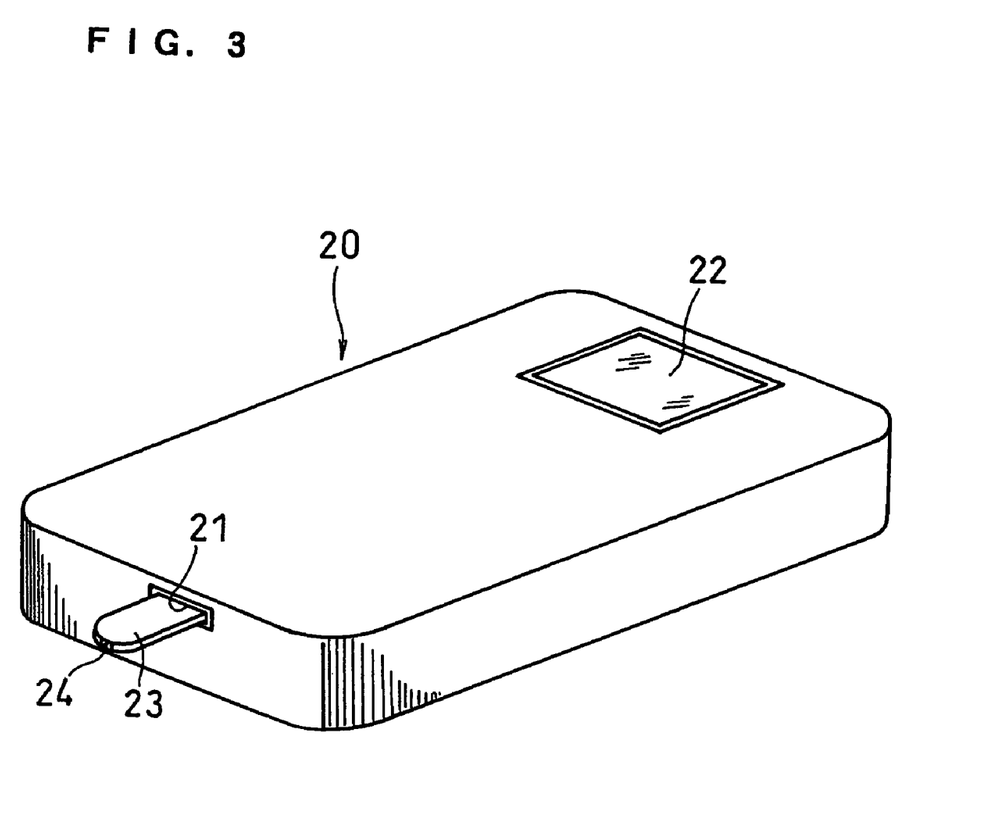
FIG. 3 is an oblique view of a measuring instrument loaded with a biosensor according to Embodiment 1 of the present invention.

FIG. 3 shows a body fluid measuring instrument 20. This figure shows a state where a biosensor 23 is loaded in an insertion hole 21 for accepting the biosensor. The measuring instrument 20 measures a blood glucose level in blood supplied to the biosensor 23 with the biosensor 23 and shows the measurement result in a display section 22. The biosensor 23 includes a body fluid supply port 24 to which blood is supplied, a supply pathway for accepting the blood from the body fluid supply port by capillary action, a reagent layer provided in the supply pathway and a pair of electrodes. The reagent layer contains an enzyme reacting with a substrate in the supplied blood, e.g., glucose. Further, the reagent preferably includes an electron mediator. A structure of a biosensor of this kind and a method of measuring the substrate using the same are disclosed, for example, in a specification of U.S. Pat. No. 5,120,420, which are well known among those skilled in the art.

An adaptor for measurement 30 according to Embodiment 1 of the present invention is preferably of a size that can be held in one hand. The adaptor for measurement 30 includes a puncture instrument holding section 31 for detachably carrying the puncture instrument 10 and a measuring instrument holding section 32 for detachably carrying the body fluid measuring instrument 20, both being isolated by a partition 33. The puncture instrument holding section 31 forms a cylinder provided with a slit 35 that fits the outside shape of a barrel of the puncture instrument 10 in cooperation with a projection 34 extending from the partition 33. A hollow part 36 in the cylinder has a diameter slightly smaller than a diameter of the barrel of the puncture instrument 10. When the puncture instrument 10 is forced into the hollow part 36 such that the holding section 31 is expanded in a direction of an arrow B in FIG. 5, the puncture instrument 10 is securely embraced by the holding section 31 by elasticity thereof. Therefore, the adaptor for measurement 30 is made of a material having elasticity and enough rigidity to securely embrace the puncture instrument 10 when the puncture instrument 10 is attached thereto. Examples of such a material include polystyrene based resins such as an ABS resin.

On the other hand, the measuring instrument holding section 32 is configured to embrace both sides of the body fluid measuring instrument 20 fitted into a hollow part 39 with an embrace lug 38 provided at one end thereof and a projection 37 extending from the partition 33. The embrace lug 38 is configured to have a slightly smaller width than a width of the measuring instrument 20 such that the embrace lug 38 expands outwardly in a direction of an arrow C in FIG. 5 when the measuring instrument is forced into the hollow part 39 as is the case with the holding section 31 to securely embrace the measuring instrument 20 by an elastic force thereof.

Figure 7:
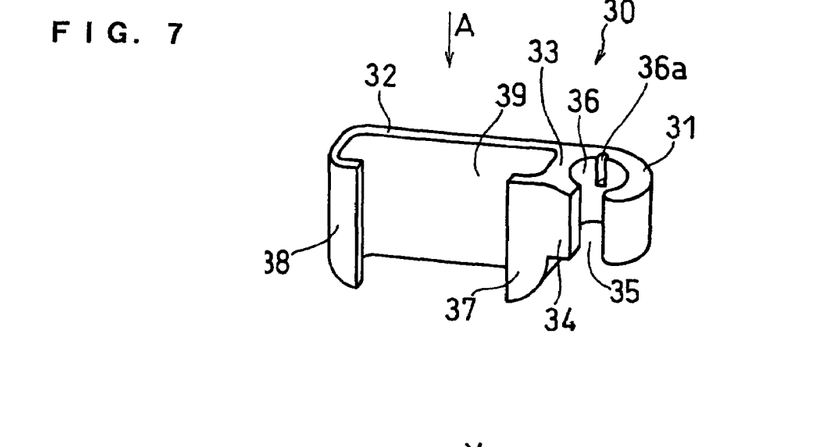
FIG. 7 is an oblique view illustrating a variant of the adaptor for measurement.

If a convex portion (not shown) is formed on the case 11 of the puncture instrument 10 on the opposite side of the button 12 and a concave portion 36a to fit with the convex portion of the puncture instrument 10 is formed on the inner surface of the holding section 31 of the adaptor 30 as shown in FIG. 7, the button 12 of the puncture instrument can be aligned with the slit 35 in attaching the puncture instrument 10 to the holding section 31. It may be possible to form the convex portion on the holding section 31 and the concave portion corresponding to the convex portion on the puncture instrument. In the same manner, the convex portion may be arranged in one of the holding section 32 and the measuring instrument and the concave portion corresponding to the convex portion may be arranged in the other.

The adaptor for measurement 30 according to this embodiment carries the puncture instrument 10 and the measuring instrument 20 on the holding sections 31 and 32, respectively, in the above-described manner. FIG. 6 shows the adaptor in this state.

Hereinbelow, explanation is given of operational procedures for collecting blood and measuring a blood glucose level thereof.

First, a disposable puncture needle 14 is loaded into the puncture instrument 10 by a user. Meanwhile, the biosensor 23 is loaded into the insertion hole 21 of the measuring instrument 20. Then, by the user, the puncture instrument 10 is attached to the puncture instrument holding section 31 from above in FIG. 4 and the measuring instrument 20 is attached to the measuring instrument holding section 32 along a direction of an arrow A in FIG. 4 (the state shown in FIG. 6). It is preferred that the puncture instrument 10 be attached such that at least one fingertip is placed on the operation button 12 when the adaptor for measurement 30 is held in one hand. For example, if a thumb is laid over the operation button 12 and the side surface of the puncture instrument holding section 31 to serve as a holding point and the other fingers are laid on the opposite side surface of the measuring instrument holding section 32 to serve as another holding point, the operation button 12 can be actuated while holding the adaptor 30 in one hand.

Then, the adaptor 30 carrying the puncture instrument 10 and the measuring instrument 20 is held in the user's dominant hand and the tip of the case 11 of the puncture instrument 10 is pressed against a body part from which the user intends to ooze blood such as a fingertip of the other hand or the other arm. At this time, the puncture needle 14 is held in the inside of the case 11. When the user presses the operation button 12 of the puncture instrument 10 by the fingertip holding the adaptor for measurement 30 to release the needle holder 17 from the stopper 19, the puncture needle 14 protrudes swiftly through the aperture 15 in the cover 13 on the tip of the case 11. Thereby, the fingertip or the arm is pricked by the puncture needle 14 to allow the blood to ooze.

Subsequently, holding the adaptor for measurement 30 carrying the puncture instrument 10 and the measuring instrument 20 in the dominant hand, the user slides the adaptor 30 such that the body fluid supply port 24 at the tip of the biosensor 23 contacts the oozed blood. Thereby, the oozed blood is supplied to the tip of the biosensor 23 and introduced in the sensor. When the blood is supplied into the biosensor 23 in an amount sufficient for measurement, reaction proceeds between glucose in the blood and the enzyme in the reaction layer of the biosensor 23. After a predetermined time has passed, the measuring instrument 20 applies a voltage to the electrode pair in the biosensor 23. Thereby, an electric current flows in response to the glucose concentration based on the reaction in the biosensor 23. The measuring instrument measures the electric current, calculates the glucose concentration from the electric current value and shows the glucose concentration in the display section 22. Thus, the measurement is completed.

In Embodiment 1 of the present invention, there is a difference from conventional measurement in that the blood glucose level is measured using the adaptor 30 carrying the puncture instrument 10 and the measuring instrument 20. Thereby, the user does not have to replace the puncture instrument 10 with the measuring instrument 20 during the measurement, which makes the measurement easy. Further, after oozing, the blood can promptly be supplied into the biosensor, which prevents drying of blood that may cause a measurement error. Moreover, the puncture instrument 10 and the measuring instrument 20 which the user is accustomed to use can be used as they are by attaching them to the adaptor 30.

In Embodiment 1 of the present invention, the puncture instrument 10 and the measuring instrument 20 are separated, which brings about the following advantages. That is, if the puncture operation does not succeed and the oozed blood is insufficient, the puncture operation can be redone by merely replacing the puncture needle 14 with a new one while the biosensor remained as it is. Therefore, the sensor is not wasted, which reduces the cost required for the measurement. If a problem occurs in the blood supply to the sensor even though the puncture is achieved with reliability, the biosensor only is replaced and the blood is allowed to ooze from the same puncture spot without need of repeating the puncture. Therefore, the puncture needle is not wasted and pain by the puncture is caused only one time. Moreover, also in an inpatient ward or a diagnosis field, body fluids from many patients can be measured by the same measuring instrument by replacing only the puncture instrument to which blood is adhered.

EMBODIMENT 2

Figure 8:
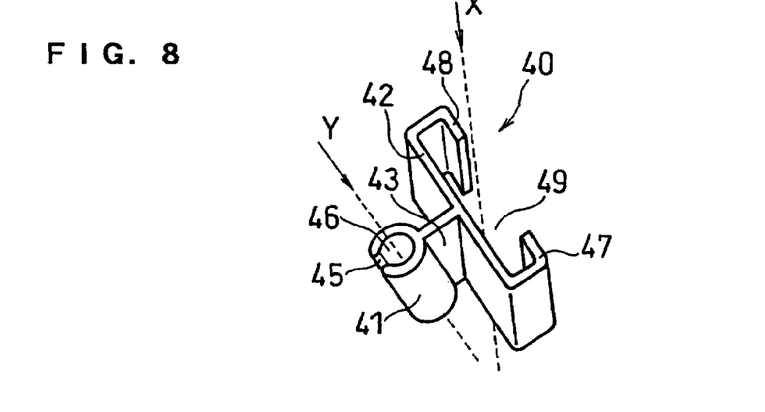
FIG. 8 is an oblique view of an adaptor for measurement according to Embodiment 2 of the present invention.

FIG. 8 shows an adaptor for measurement 40 according to Embodiment 2.

Figure 9:
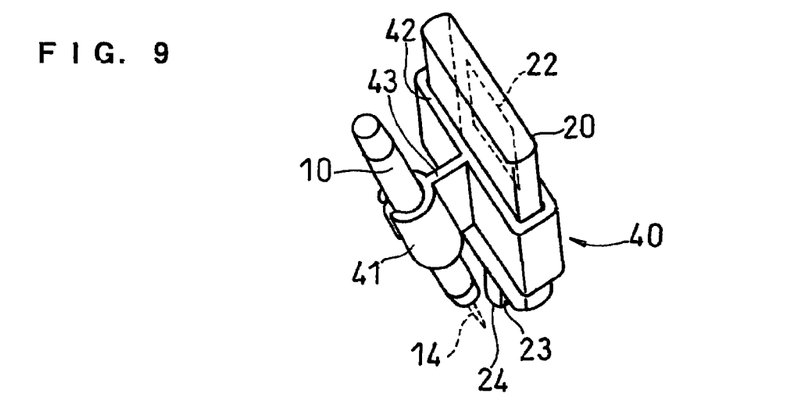
FIG. 9 is a plan view of the adaptor for measurement according to Embodiment 2 of the present invention.

The adaptor for measurement 40 includes a cylindrical puncture instrument holding section 41 having a slit 45, a measuring instrument holding section 42 having embrace lugs 47 and 48 and a lug 43 connecting the both. The adaptor is designed such that an axis Y of a hollow part 46 of the puncture instrument holding section 41 and an axis X of a hollow part 49 of the measuring instrument holding section 42 intersect with each other below the adaptor 40. FIG. 9 shows a state where a puncture instrument 10 and a measuring instrument 20 same as those of Embodiment 1 are attached to the adaptor 40.

The adaptor 40 of this embodiment is different from the adaptor for measurement 30 of Embodiment 1 in the following points.

1) The puncture instrument holding section 41 is arranged on the back of the measuring instrument holding section 42.

2) The puncture instrument holding section 41 is arranged such that a mounting direction of the puncture instrument 10 (a direction of an arrow Y in FIG. 8) forms an acute angle with a mounting direction of the measurement instrument 20 (a direction of an arrow X in FIG. 8).

Owing to these, when the puncture needle 14 of the puncture instrument 10 carried by the holding section 41 is protruded, the puncture needle 14 comes close to the body fluid supply port 24 of the biosensor 23 loaded in the biosensor insertion hole 21. It is preferable to determine the relative positions of the puncture instrument holding section 41 and the measuring instrument holding section 42 such that the tip of the puncture needle 14 and the body fluid supply port 24 become close within an area of about a single ball of a finger. Thereby, the blood is allowed to ooze by the puncture instrument 10 and then introduced to the biosensor 23 while retaining the adaptor 40 as it is, without sliding. Thus, the user can conduct the measurement easily and speedily.

EMBODIMENT 3

Figure 10:
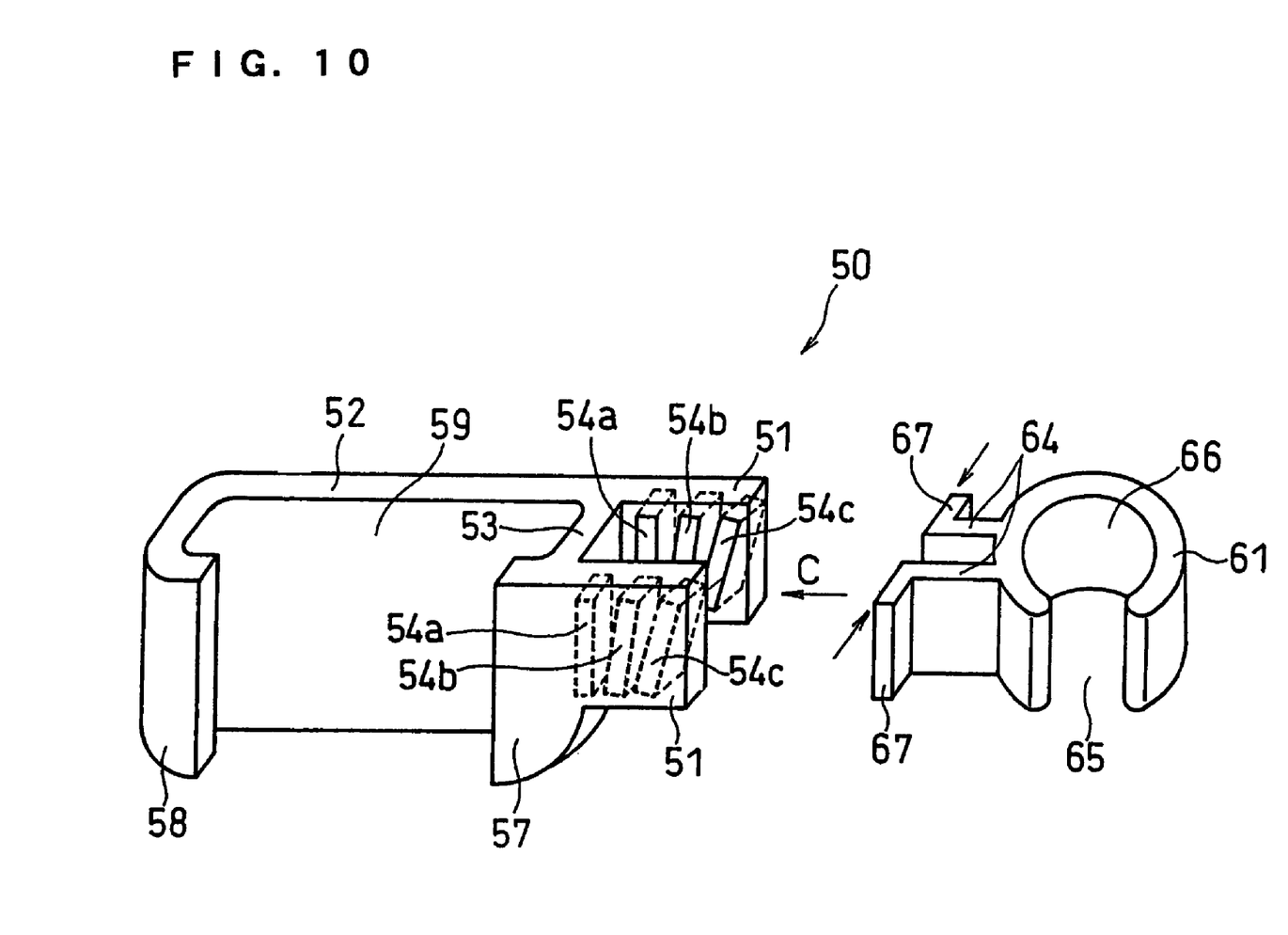
FIG. 10 is an oblique view illustrating a state where the puncture instrument and the measuring instrument are attached to an adaptor for measurement according to Embodiment 3 of the present invention.

FIG. 10 shows an adaptor 50 according to this embodiment.

The adaptor 50 is made of an elastic synthetic resin as is the case of Embodiment 1. A puncture instrument holding section 61 and a measuring instrument holding section 52 are formed separately, but they are joined in use as described below. The puncture instrument holding section 61 is made of a cylinder having a slit 65 and includes a pair of joint lugs 64 formed on the side surface. Each of the lugs 64 has a projection 67 bended outwardly at the tip thereof. On the other hand, the measuring instrument holding section 52 has embrace lugs 57 and 58 for embracing the side surface of the measuring instrument. A partition 53 extending to the embrace lug 57 has a pair of joint lugs 51 formed on the side surface. On the surfaces of the lugs 51 opposing to each other, three pairs of convex portions 54a, 54b and 54c are arranged. These convex portions are angled differently with respect to the partition 53, i.e., to the measuring instrument to be attached to the holding section 52. That is, the angle formed by the partition 53 and these convex portions, respectively, increases in the order of the convex portions 54a, 54b and 54c.

In joining the puncture instrument holding section 61 and the measuring instrument holding section 52, the paired lugs 64 are pinched between fingertips from the outer side to move the projections 67 in the direction of arrows shown in the figure. Then, the projections 64 are fitted into any one of the convex portions 54a, 54b and 54c of the joint lugs 51 of the measuring instrument holding section 52 and the force of the fingertips pinching the lugs 64 is eased. In this way, by fitting the projections 67 completely in any of the convex portions, the puncture instrument holding section 61 and the measuring instrument holding section 52 are joined in one piece to be put into use. Depending on which of the convex portions 54a, 54b and 54c the projections 67 of the puncture instrument holding section are fitted into, is adjusted a distance between the biosensor of the measuring instrument 20 carried by the holding section 52 and the puncture needle protruding from the puncture instrument 10 carried by the holding section 61. In this way, the convex portions 54a, 54b and 54c of the joint lugs 51 serve as an angle adjustor for adjusting a mounting angle of the puncture instrument holding section 61. The puncture instrument and the measuring instrument are fitted into hollow parts 66 and 59 of the holding sections 61 and 52, respectively, in the same manner as the foregoing embodiments.

The shape of the puncture instrument is not limited to the one disclosed in the foregoing embodiments as long as the puncture instrument has a function of protruding the puncture needle. Also, the puncture instrument holding section of the adaptor to which the puncture instrument is attached is not limited to the shape described above as long as it is shaped to be able to carry the puncture instrument detachably, preferably embrace the puncture instrument fitted therein. In the same manner, the shape of the measuring instrument is not limited to the one described above as long as the measuring instrument has a function of measuring a substrate by the biosensor loaded therein. The measuring instrument holding section of the adaptor to which the measuring instrument is attached is not limited to the shape described above as long as it is shaped to be able to carry the measuring instrument detachably, preferably embrace the measuring instrument fitted therein.

Further, the biosensor and the measuring instrument are not limited to those disclosed above. For example, a measuring instrument using a sensor having a reagent layer containing an enzyme and a dye which changes color through the enzyme reaction may be used to determine the content of a substrate by optically measuring the color change of the dye.

EMBODIMENT 4

In this embodiment, explanation is given of a body fluid measuring instrument which is allowed to carry a puncture instrument, i.e., a measuring instrument integrated in one piece with the above-described adaptor.

Figure 11:
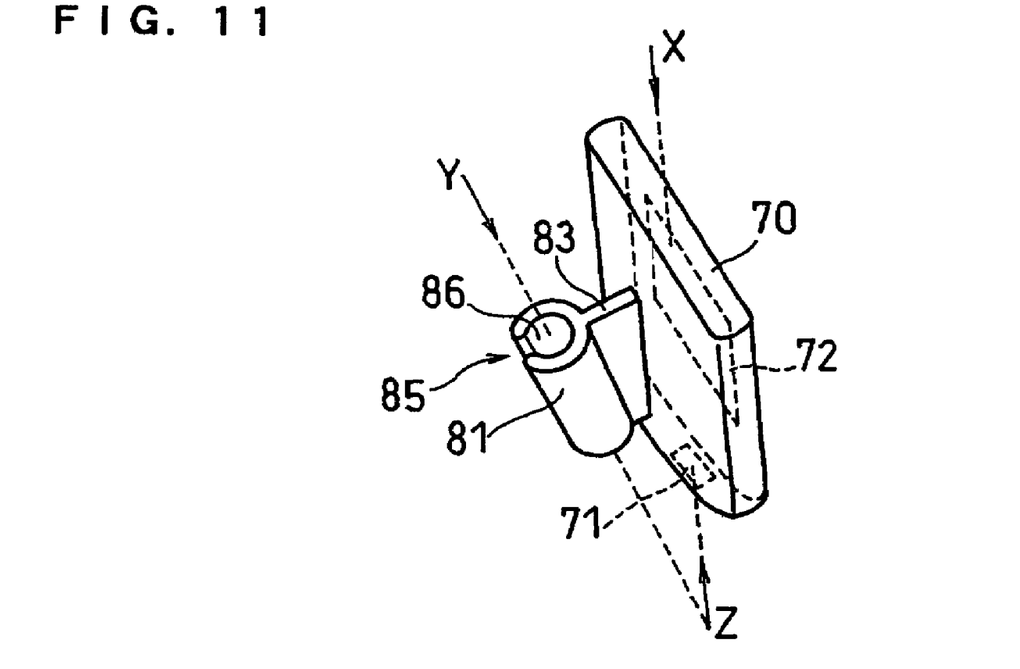
FIG. 11 is an oblique view of a body fluid measuring instrument according to Embodiment 4 of the present invention.
Figure 12:
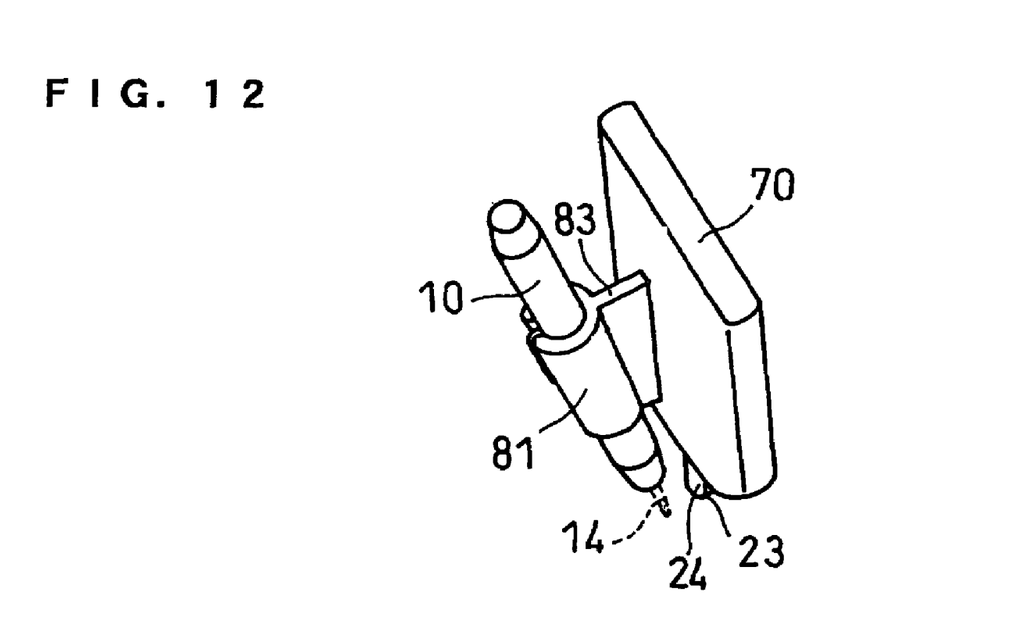
FIG. 12 is an oblique view illustrating a state where the puncture instrument is attached to the measuring instrument according to Embodiment 4 of the present invention.

FIGS. 11 and 12 show a body fluid measuring instrument 70 according to this embodiment.

The measuring instrument 70 is preferably of a size that can be held in one hand. The measuring instrument 70 includes an insertion hole 71 for loading a biosensor 23 therein and a display section 72 for showing the measurement result. Further, via a support lug 83, a puncture instrument holding section 81 is integrated onto the surface opposite to the surface where the display section 72 is formed. The puncture instrument holding section 81 is made of an elastic synthetic resin as is the case with the foregoing embodiments and configured as a cylinder provided with a slit 85 to embrace the barrel of the puncture instrument in a hollow part 86. That is, the hollow part 86 is configured to have a diameter slightly smaller than a diameter of the barrel of the puncture instrument 10 such that the holding section 81 is expanded to fit and hold the puncture instrument therein. The puncture instrument 10 and the biosensor 23 are the same as those of Embodiment 1.

The puncture instrument holding section 81 is preferably arranged on the measuring instrument such that the puncture needle 14 protruding from the puncture instrument 10 embraced therein comes close to the body fluid supply port 24 provided at the tip of the biosensor 23 loaded in the biosensor insertion hole 21, preferably comes close to the body fluid supply support 24 within an area of about a single ball of a finger.

In the same manner as the above embodiment, if a convex or concave portion is formed on the barrel of the puncture instrument 10 and a corresponding concave or convex portion is formed on the inner surface of the holding section 81, it is convenient for positioning the puncture instrument in attaching the puncture instrument.

How to use the body fluid measuring instrument is the same after the puncture instrument is attached to the holding section 81 as the adaptor carrying the puncture instrument and the measuring instrument described in the above embodiment.

According to the body fluid measuring instrument of the present invention, a user does not have to replace the puncture instrument during the measurement, which makes the measurement easy. Further, since the puncture position of the puncture instrument is close to the body fluid supply port of the biosensor, the blood can promptly be supplied into the biosensor after oozing, which prevents drying of blood that may cause a measurement error.

The biosensor and the measuring instrument are not limited to those disclosed in the present embodiments. For example, a measuring instrument using a sensor having a reagent layer containing an enzyme and a dye which changes color through the enzyme reaction may be used to determine the content of a substrate by optically measuring the color change of the dye.

In the above, explanation is given of the measurement of the blood glucose level in human blood. However, the present invention is not limited thereto. By selecting the puncture needle or a body part to be pricked, for example, intercellular fluid may be targeted as the body fluid other than blood. Further, by selecting the biosensor and the measuring instrument as appropriate depending on the target to be analyzed, it is also allowed to detect the existence of a specific substance in the body fluid such as virus or measure the content of substrates in the body fluid such as glucose, cholesterol and lactic acid.

INDUSTRIAL APPLICABILITY

According to the present invention, measurement can be conducted easily and speedily by a user even if the puncture instrument and the measuring instrument are separated.

The invention claimed is:

1. A system for body fluid measurement comprising:
a puncture needle;
a puncture instrument for protruding the puncture needle;
a biosensor having a body fluid supply part to which body fluid is supplied;
a measuring instrument having a biosensor holding section for holding the biosensor; and
an adapter comprising:
a puncture instrument holding section for detachably carrying the puncture instrument; and
a measuring instrument holding section for detachably carrying the measuring instrument,
wherein the puncture instrument holding section and the measuring instrument holding section are configured such that an axis of the puncture needle of the puncture instrument carried by the puncture instrument holding section intersects with an axis of an inserting direction of the biosensor attached to the measuring instrument carried by the measuring instrument holding section.

2. The system in accordance with claim 1, further comprising an adjustment part for adjusting an angle of the puncture instrument holding section with respect to the measuring instrument holding section, wherein said adjustment part is located between said measuring instrument holding section and said puncture instrument holding section.

3. The system in accordance with claim 1,
wherein the puncture instrument holding section includes an embrace part for embracing a barrel of the puncture instrument, said embrace part being attached to said measuring instrument holding section.

4. The system in accordance with claim 3,
wherein the embrace part comprises a cylinder provided with a slit, said slit being aligned vertically with respect to the cylinder axis, the cylinder being configured to have a diameter slightly smaller than a diameter of the barrel of the puncture instrument to embrace the barrel of the puncture instrument by an elastic force thereof.

5. The system in accordance with claim 3,
wherein the puncture instrument holding section has a concave portion or a convex portion to fit with a convex portion or a concave portion formed on the barrel of the puncture instrument.

6. A system for body fluid measurement comprising:
a puncture needle;
a puncture instrument for protruding the puncture needle;
a biosensor having a body fluid supply part to which body fluid is supplied;
a measuring instrument comprising:
a biosensor holding section for holding the biosensor; and
a puncture instrument holding section for detachably carrying the puncture instrument,
wherein the puncture instrument holding section and the biosensor holding section are configured such that an axis of the puncture needle of the puncture instrument carried by the puncture instrument holding section intersects with an axis of an inserting direction of the biosensor attached to the biosensor holding section, and
wherein the puncture instrument holding section has an embrace part for embracing a barrel of the puncture instrument, said embrace part being attached to said measuring instrument.

7. The system in accordance with claim 6,
wherein the embrace part comprises a cylinder provided with a slit, said slit being aligned vertically with respect to the cylinder axis, the cylinder being configured to have a diameter slightly smaller than a diameter of the barrel of the puncture instrument to embrace the barrel of the puncture instrument by an elastic force thereof.

8. A system for body fluid measurement comprising:
a puncture needle;
a puncture instrument for protruding the puncture needle;
a biosensor having a body fluid supply part to which body fluid is supplied;
a measuring instrument comprising:
a biosensor holding section for holding the biosensor; and
a puncture instrument holding section for detachably carrying the puncture instrument,
wherein the puncture instrument holding section and the biosensor holding section are configured such that an axis of the puncture needle of the puncture instrument carried by the puncture instrument holding section intersects with an axis of an inserting direction of the biosensor attached to the biosensor holding section,
wherein the puncture instrument holding section has a concave portion or a convex portion to fit with a convex portion or a concave portion formed on the barrel of the puncture instrument.

* * * * *

UNITED STATES PATENT AND TRADEMARK OFFICE
CERTIFICATE OF CORRECTION

PATENT NO.       : 7,252,804 B2
APPLICATION NO.  : 10/472209
DATED            : August 7, 2007
INVENTOR(S)      : Mariko Miyashita et al.

It is certified that error appears in the above-identified patent and that said Letters Patent is hereby corrected as shown below:

On the title page of the Letters Patent:

Item (56) references cited, add:

-- Foreign Patent Documents

JP  P2001-245872  09/2001
JP   2001-524680  12/2001
JP  P2000-152923  06/2000
JP  P2001-170031  06/2001 --

Signed and Sealed this

Twentieth Day of May, 2008

JON W. DUDAS
*Director of the United States Patent and Trademark Office*